United States Patent [19]

Föry et al.

[11] Patent Number: 5,336,773
[45] Date of Patent: Aug. 9, 1994

[54] CERTAIN-3-AMINO-2-PYRIDINE-SULFONAMIDE INTERMEDIATES

[75] Inventors: Werner Föry, Riehen; Rolf Schurter, Binningen, both of Switzerland

[73] Assignee: Ciba-Geigy Corporation, Ardsley, N.Y.

[21] Appl. No.: 43,231

[22] Filed: Apr. 6, 1993

Related U.S. Application Data

[62] Division of Ser. No. 705,459, May 24, 1991, Pat. No. 5,221,315.

[30] Foreign Application Priority Data

May 30, 1990 [CH] Switzerland ............... 1826/90

[51] Int. Cl.$^5$ ................ C07D 213/69; C07D 213/70
[52] U.S. Cl. ........................ 546/294; 544/212; 544/331
[58] Field of Search ........................... 546/294

[56] References Cited

U.S. PATENT DOCUMENTS

| | | | |
|---|---|---|---|
| 4,480,101 | 10/1984 | Meyer | 544/320 |
| 4,537,619 | 8/1985 | Meyer et al. | 71/93 |
| 4,544,401 | 10/1985 | Levitt | 71/92 |
| 4,579,583 | 4/1986 | Fory et al. | 71/92 |
| 4,657,578 | 2/1987 | Thompson | 71/90 |
| 4,707,179 | 11/1987 | Thompson | 71/90 |
| 4,746,353 | 5/1988 | Levitt | 71/90 |
| 4,789,465 | 12/1988 | Barnette et al. | 71/90 |

OTHER PUBLICATIONS

Chemical Abstracts, vol. 102 (No. 7) Abst. No. 102:62050-Z (Feb. 18, 1985).
J. Pharm. Belg. (1984), vol. 39, (4), pp. 217–224.
Farmaco Ed., Scient., vol. 12, 392 (1957), pp. 387–393.

*Primary Examiner*—Alan L. Rotman
*Attorney, Agent, or Firm*—Kevin T. Mansfield; Edward McC. Roberts

[57] ABSTRACT

N-Pyridinesulfonyl-N'-pyrimidinyl- and -triazinylureas of the formula I

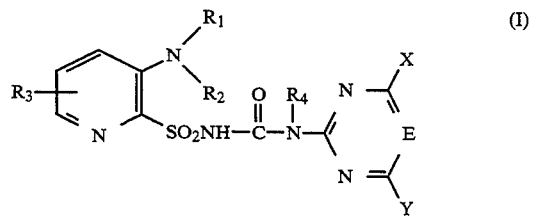

in which $R_1$ and $R_2$ independently of one another are hydrogen, $C_1$–$C_8$alkyl or $C_3$–$C_8$cycloalkyl; $C_2$–$C_8$alkyl or $C_3$–$C_8$cycloalkyl, each of which is monosubstituted or polysubstituted by halogen; $C_1$–$C_8$alkyl or $C_3$–$C_8$cycloalkyl, each of which is substituted by —$NR_5R_6$, $C_1$–$C_4$alkoxy or $C_1$–$C_4$alkyl—$S(O)_n$—; $C_1$–$C_4$alkyl or $C_3$–$C_6$cycloalkyl, each of which is substituted by $C_2$–$C_4$alkenyl, $C_5$–$C_6$cycloalkenyl, $C_2$–$C_6$alkynyl or $C_4$–$C_8$alkadienyl; it being possible for the $C_2$–$C_4$alkenyl, $C_5$–$C_6$cycloalkenyl and $C_4$–$C_8$alkadienyl radicals to be monosubstituted or polysubstituted by halogen; or $R_1$ and $R_2$ together are a 4–5-membered $C_4$–$C_{10}$alkylene chain which can be interrupted by oxygen, sulfur or N—$R_7$; $R_3$ is hydrogen, halogen, $C_1$–$C_4$alkyl, $C_1$–$C_4$alkoxy or $C_1$–$C_4$alkylthio; $C_1$–$C_4$alkyl, $C_1$–$C_4$alkoxy or $C_1$–$C_4$alkylthio, each of which is monosubstituted or polysubstituted by halogen; $R_4$, $R_5$, $R_6$ and $R_7$ independently of one another are hydrogen or $C_1$–$C_4$alkyl; n is 0, 1 or 2; X is $C_1$–$C_3$alkyl, or $C_1$–$C_3$alkyl which is monosubstituted to trisubstituted by halogen; $C_1$–$C_3$alkoxy, or $C_1$–$C_3$alkoxy which is monosubstituted to trisubstituted by halogen; Y is halogen, $C_1$–$C_3$alkyl or $C_1$–$C_3$alkyl which is monosubstituted to trisubstituted by halogen; $C_1$–$C_3$alkoxy, or $C_1$–$C_3$alkoxy which is monosubstituted to trisubstituted by halogen; cyclopropyl, methylamino or dimethylamino; and E is nitrogen or the methine group, and the salts of these compounds with amines, alkali metal bases or alkaline earth metal bases or with quaternary ammonium bases have good selective herbicidal and growth-regulating properties when used pre- and post-emergence.

9 Claims, No Drawings

CERTAIN-3-AMINO-2-PYRIDINE-SULFONAMIDE INTERMEDIATES

This is a Divisional of Ser. No. 07/705,459, filed May 24, 1991 U.S. Pat. No. 5,221,315.

The present invention relates to novel, herbicidally active and plant-growth-regulating N-pyridinesulfonyl-N'-pyrimidinyl- and -triazinylureas, processes for their preparation, compositions containing them as active substances, and their use for controlling weeds, especially selectively in crops of useful plants or for regulating and inhibiting plant growth.

Urea compounds, triazine compounds and pyrimidine compounds which have a herbicidal action are generally known. For example, European Patent No. 103 543 and U.S. Pat. No. 4,544,401 describe herbicidally active and plant-growth-regulating N-pyridinesulfonyl-N'-pyrimidinyl- and -triazinylureas. However, the active substances disclosed therein cannot always meet the requirements as far as power and selectivity are concerned. There is hence a demand for active substances which have a better activity and are more selective.

Novel sulfonylureas which have improved herbicidal and plant-growth-regulating properties have now been found.

The N-pyridinesulfonyl-N'-pyrimidinyl- and triazinylureas according to the invention are those of the formula I

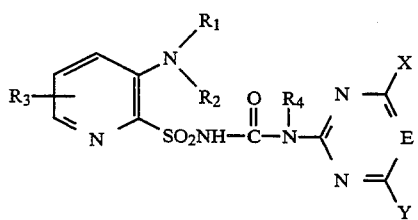

in which $R_1$ and $R_2$ independently of one another are hydrogen, $C_1$–$C_8$alkyl or $C_3$–$C_8$cycloalkyl; $C_2$–$C_8$alkyl or $C_3$–$C_8$cycloalkyl, each of which is monosubstituted or polysubstituted by halogen; $C_1$–$C_8$alkyl or $C_3$–$C_8$cycloalkyl, each of which is substituted by $-NR_5R_6$, $C_1$–$C_4$alkoxy or $C_1$–$C_4$alkyl—$S(O)_n$—; $C_1$–$C_4$alkyl or $C_3$–$C_6$cycloalkyl, each of which is substituted by $C_2$–$C_4$alkenyl, $C_5$–$C_6$cycloalkenyl, $C_2$–$C_6$alkynyl or $C_4$–$C_8$alkadienyl; it being possible for the $C_2$–$C_4$alkenyl, $C_5$–$C_6$cycloalkenyl and $C_4$–$C_8$alkadienyl radicals to be monosubstituted or polysubstituted by halogen; or $R_1$ and $R_2$ together are a 4–5-membered $C_4$–$C_{10}$alkylene chain which can be interrupted by oxygen, sulfur or N—$R_7$; $R_3$ is hydrogen, halogen, $C_1$–$C_4$alkyl, $C_1$–$C_4$alkoxy or $C_1$–$C_4$alkylthio; $C_1$–$C_4$alkyl, $C_1$–$C_4$alkylthio, each of which is monosubstituted or polysubstituted by halogen; $R_4$, $R_5$, $R_6$ and $R_7$ independently of one another are hydrogen or $C_1$–$C_4$alkyl; n is 0, 1 or 2; X is $C_1$–$C_3$alkyl, or $C_1$–$C_3$alkyl which is monosubstituted to trisubstituted by halogen; $C_1$–$C_3$alkoxy, or $C_1$–$C_3$alkoxy which is monosubstituted to trisubstituted by halogen; Y is halogen, $C_1$–$C_3$alkyl or $C_1$–$C_3$alkyl which is monosubstituted to trisubstituted by halogen; $C_1$–$C_3$alkoxy, or $C_1$–$C_3$alkoxy which is monosubstituted to trisubstituted by halogen; cyclopropyl, methylamino or dimethylamino; and E is nitrogen or the methine group, and the salts of these compounds.

The alkyl groups which occur as, or in, the substituents $R_1$ to $R_7$ can be straight-chain or branched and are, for example, methyl, ethyl, n-propyl, iso-propyl, n-butyl, sec-butyl, iso-butyl, tert-butyl, n-pentyl or the pentyl isomers, n-hexyl or the hexyl isomers, n-heptyl or the heptyl isomers, and also n-octyl or the octyl isomers. The alkyl groups which occur as, or in, the substituents preferably have 1–4 carbon atoms.

The alkyl groups which are monosubstituted or polysubstituted by halogen and which occur as, or in, the substituents $R_1$–$R_3$ embrace straight-chain or branched alkyl groups such as methyl, ethyl, n-propyl, iso-propyl, n-butyl, sec-butyl, iso-butyl, tert-butyl, n-pentyl, the pentyl isomers, n-hexyl as well as the hexyl isomers, n-heptyl or the heptyl isomers, as well as n-octyl or the octyl isomers, each of these groups being monosubstituted or polysubstituted by halogen, halogen specifically meaning fluorine, chlorine, bromine or iodine.

From amongst these alkyl groups which are monosubstituted or polysubstituted by halogen, alkyl groups which are monosubstituted to trisubstituted by halogen are preferred. Preferred halogen atoms which can occur as substituents of the alkyl groups are fluorine and chlorine. Especially preferred alkyl groups which are monosubstituted or polysubstituted by halogen are trifluoromethyl, 1-fluoroethyl, 1,1-dichloroethyl, 3,3,3-trifluoropropyl, 2-fluoroisopropyl, 3-fluoropropyl, 1,1,1-trichloropentyl, 1-fluoro-3-methylpentyl or 1-bromohexyl. 3-Fluoropropyl and 2-fluoroisopropyl are very particularly preferred.

The $C_1$–$C_3$alkyl radicals which occur as, or in, the substituents X and Y specifically embrace methyl, ethyl, n-propyl and iso-propyl, as well as the haloalkyls which are monosubstituted to trisubstituted by halogen and which are derived from these radicals. The alkyl radicals which occur as, or in, the substituents X and Y preferably have one to two carbon atoms.

Preferred groups amongst the $C_1$–$C_3$alkyl groups which are monosubstituted to trisubstituted by halogen and which occur as, or in, the substituents X and Y are $C_1$–$C_2$alkyl groups which are monosubstituted to trisubstituted by fluorine or chlorine. Especially preferred $C_1$–$C_3$alkyl radicals which are monosubstituted to trisubstituted by halogen and which occur as, or in, the substituents X and Y are: trifluoromethyl, difluoromethyl, 2-chloroethyl, chlorodifluoromethyl, dichloromethyl, chlorofluoromethyl, 1,1-dichloroethyl, trifluoroethyl, 3,3,3-trifluoropropyl or 2,3-dichloropropyl, particularly preferred are fluoromethyl, chloromethyl, difluoromethyl and trifluoromethyl.

The $C_2$–$C_4$alkenyl radicals which occur in the substituents $R_1$ and $R_2$ can be in the Z form (cis) or in the E form (trans) and can be straight-chain or branched. Preferred alkenyl radicals are those having a chain length of two to three carbon atoms. Examples of $C_2$–$C_4$alkenyl radicals are: vinyl, allyl, methallyl, 1-methylvinyl and but-2-en-1-yl. Vinyl and allyl are preferred. In the case of the $C_2$–$C_4$alkenyl radicals which are monosubstituted or polysubstituted by halogen, halogen is, specifically, fluorine, chlorine, bromine and iodine. Preferred halogen atoms which can occur as substituents of the $C_2$–$C_4$alkenyl radicals are fluorine and chlorine. Preferred radicals amongst the $C_2$–$C_4$alkenyl radicals which are monosubstituted to trisubstituted by halogen are those which have a chain length of two to three carbon atoms. Especially preferred $C_2$–$C_4$alkenyl radicals which are monosubstituted to trisubstituted by halogen are 1-chlorovinyl, 2-chlorovinyl, 3-fluoroallyl and 4,4,4-trifluoro-but-2-en-1-yl. 1-Chlorovinyl and 2-chlorovinyl are very particularly preferred.

The $C_4$–$C_8$alkadienyl radicals which can be monosubstituted or polysubstituted by halogen and which occur in the substituents $R_1$ and $R_2$ are, for example, buta-1,3-dienyl, penta-1,3-dienyl, hexa-3,5-dienyl, hepta-4,6-dienyl, octa-1,7-dienyl, 4-chlorobuta-1,3-dienyl, or 5,5,5-trifluoropenta-1,3-dienyl.

The $C_2$–$C_6$alkynyl radicals which occur in the definitions of the substituents $R_1$ and $R_2$ can be straight-chain or branched. Preferred alkynyl radicals are those which have a chain length of two to three carbon atoms. $C_2$–$C_4$Alkynyl radicals are, for example, ethynyl, propargyl, 1-propynyl, 3-butynyl, 1-methylpropargyl, 3-pentynyl or 3-hexynyl, ethynyl and propargyl being particularly preferred.

The cycloalkyl groups which are unsubstituted or monosubstituted or polysubstituted by halogen and which occur in the substituents $R_1$ and $R_2$ embrace, for example, cyclopropyl, cyclobutyl, cyclopentyl, cyclohexyl, cycloheptyl, cyclooctyl, 2-fluorocyclopropyl, 2,3-diflurocyclopropyl, 2,2-dichlorocyclopropyl, 3-bromocyclopropyl, 2,3,4-trifluorocyclopentyl or 2,3-dichlorocyclohexyl. Preferred amongst these cycloalkyl groups are the cyclopropyl, cyclopentyl and cyclohexyl groups which are monosubstituted to disubstituted by halogen, halogen being fluorine, chlorine, bromine and iodine, but in particular fluorine and chlorine.

Examples of other substituted cycloalkyl groups are 2-methoxycyclopropyl, 3-ethylthiocyclobutyl, 2-methylsulfonylcyclopentyl, 3-ethylsulfinylcyclohexyl, 4-(2,4-pentadienyl)-cyclohexane, 3-aminocyclohexyl, 4-allylcyclohexyl or 3-propargylcyclohexyl.

The $C_5$–$C_6$cycloalkenyl radicals can be monosubstituted to trisubstituted by halogen. Preferred halogen atoms here are fluorine and chlorine. Examples of $C_5$–$C_6$cycloalkenyl radicals are 3-cyclopentene, 2-cyclopentene, 4-chlorocyclopent-3-ene, 3,4-difluorocyclopent-3-ene, 2-cyclohexene, 3-cyclohexene, 4,5-dibromocyclohex-2-ene or 4,4,5-trifluorocyclohex-2-ene.

Examples of heterocycles which can, together with the nitrogen atom to which they are bonded, form the substituents $R_1$ and $R_2$ are: pyrrolidine, 3-methylpyrrolidine, imidazolidine, piperidine, 3-isopropylpiperidine, piperazine, 4-methylpiperazine, 4-ethylpiperazine, 4-isopropylpiperazine, morpholine, oxazolidine, and thiazolidine. It is preferred for the substituents $R_1$ and $R_2$ to form 4–5-membered $C_4$–$C_5$alkylene chains. Preferred heterocycles which can, together with the nitrogen atom to which they are bonded, form the substituents $R_1$ and $R_2$ are: 4-methylpiperazine, morpholine and piperidine.

Alkylthio is, for example, methylthio, ethylthio, propylthio, isopropylthio, n-butylthio, i-butylthio, s-butylthio, t-butylthio or the pentylthio isomers, preferably methylthio and ethylthio.

Alkoxy is, for example, methoxy, ethoxy, propyloxy, i-propyloxy, n-butyloxy, i-butyloxy, s-butyloxy and t-butyloxy; preferably methoxy and ethoxy.

The invention also embraces the salts which the compounds of the formula I can form together with amines, alkali metal bases and alkaline earth metal bases or quaternary ammonium bases.

Salt formers which must be emphasised amongst alkali metal hydroxides and alkaline earth metal hydroxides are the hydroxides of lithium, sodium, potassium, magnesium or calcium, but in particular those of sodium or potassium.

Examples of amines which are suitable for salt formation are primary, secondary and tertiary aliphatic and aromatic amines such as methylamine, ethylamine, propylamine, isopropylamine, the four butylamine isomers, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline, but in particular ethyl-, propyl-, diethyl- or triethylamine, but above all isopropylamine and diethanolamine.

Examples of quaternary ammonium bases are, generally, the cations of ammonium halide salts, for example the tetramethylammonium cation, the trimethylbenzylammonium cation, the triethylbenzylammonium cation, the tetraethylammonium cation, the trimethylethylammonium cation, but also the ammonium cation.

Compounds from within the scope of the formula I which must be emphasised are those in which $R_1$ and $R_2$ independently of one another are hydrogen, $C_1$–$C_8$alkyl or $C_3$–$C_8$cycloalkyl; $C_2$–$C_8$alkyl or $C_3$–$C_8$cycloalkyl which are monosubstituted or polysubstituted by halogen; $C_1$–$C_8$alkyl or $C_3$–$C_8$cycloalkyl which are substituted by —$NR_5R_6$, $C_1$–$C_4$alkoxy or $C_1$–$C_4$alkyl—$S(O)_n$—; $C_1$–$C_4$alkyl or $C_3$–$C_6$cycloalkyl which are substituted by $C_2$–$C_4$alkenyl, $C_5$–$C_6$cycloalkenyl, $C_2$–$C_6$alkynyl or $C_4$–$C_8$alkadienyl; it being possible for the $C_2$–$C_4$alkenyl, $C_5$–$C_6$cycloalkenyl and $C_4$–$C_8$alkadienyl radicals to be monosubstituted or polysubstituted by halogen.

Other preferred compounds from amongst those of the formula I are those in which $R_1$ and $R_2$ independently of one another are hydrogen, $C_1$–$C_6$alkyl or $C_3$–$C_6$cycloalkyl; $C_2$–$C_6$alkyl or $C_3$–$C_6$cycloalkyl which are monosubstituted to trisubstituted by halogen; $C_1$–$C_6$alkyl or $C_3$–$C_6$cycloalkyl which are substituted by —$NR_5R_6$, $C_1$–$C_4$alkoxy or $C_1$–$C_4$alkyl—$S(O)_n$—; $C_1$–$C_4$alkyl or $C_3$–$C_6$cycloalkyl which are substituted by $C_2$–$C_4$alkenyl, $C_5$–$C_6$cycloalkenyl, $C_2$–$C_4$alkynyl or $C_4$–$C_8$alkadienyl; it being possible for the $C_2$–$C_4$alkenyl, $C_5$–$C_6$cycloalkenyl and $C_4$–$C_8$alkadienyl radicals to be monosubstituted to trisubstituted by halogen; and $R_3$ is hydrogen, halogen, $C_1$–$C_4$alkyl, $C_1$–$C_4$alkoxy or $C_1$–$C_4$alkylthio; or $C_1$–$C_4$alkyl, $C_1$–$C_4$alkoxy or $C_1$–$C_4$alkylthio which are monosubstituted to trisubstituted by halogen.

Furthermore, compounds amongst those of the formula I which are of particular interest are those in which at least one of the substituents $R_1R_2$ and $R_3$ is other than hydrogen.

Very particularly preferred groups of compounds of the formula I are those in which a) X is $C_1$–$C_3$alkyl, $C_1$–$C_3$alkoxy or $C_1$–$C_3$alkoxy which is monosubstituted to trisubstituted by halogen; and Y is chlorine, $C_1$–$C_3$alkyl, $C_1$–$C_3$alkoxy or $C_1$–$C_3$alkoxy which is monosubstituted to trisubstituted by halogen; or b) X is methyl, methoxy, ethoxy or difluoromethoxy; and Y is methyl, methoxy, ethoxy, difluoromethoxy or chlorine; or c) X is methoxy or ethoxy; and Y is methyl or methoxy;

d) E is the methine bridge; or e) $R_3$ is in the 6-position of the pyridine ring; or f) $R_3$ is hydrogen.

From amongst these compounds, compounds in which a) $R_2$ and $R_3$ are hydrogen and $R_1$ is $C_1$-$C_6$alkyl or $C_3$-$C_6$cycloalkyl; $C_2$-$C_6$alkyl or $C_3$-$C_6$cycloalkyl which are monosubstituted to trisubstituted by halogen; $C_1$-$C_6$alkyl or $C_3$-$C_6$cycloalkyl which are substituted by —$NR_5R_6$, $C_1$-$C_4$alkoxy or $C_1$-$C_4$alkyl—$S(O)_n$—; $C_1$-$C_4$alkyl or $C_3$-$C_6$cycloalkyl which are substituted by $C_2$-$C_4$alkenyl, $C_5$-$C_6$cycloalkenyl, $C_2$-$C_4$alkynyl or $C_4$-$C_8$alkadienyl; it being possible for the $C_2$-$C_4$alkenyl, $C_5$-$C_6$cycloalkenyl and $C_4$-$C_8$alkadienyl radicals to be monosubstituted to trisubstituted by halogen; or b) $R_1$ is $C_1$-$C_6$alkyl, allyl or propargyl, and $R_2$ is hydrogen, methyl or allyl, must be particularly emphasised.

From within the scope of the formula I, mention must be made of N-(3-n-butylaminopyridin-2-ylsulfonyl)-N'-(4,6-dimethoxypyrimidin-2-yl)urea as a particularly preferred single compound.

The compounds of the formula I can be prepared by reacting a) a pyridylsulfonamide of the formula II

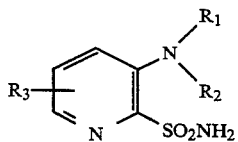
(II)

in which $R_1$, $R_2$ and $R_3$ are as defined under formula I in claim 1, with an N-pyrimidinyl or N-triazinylcarbamate of the formula III

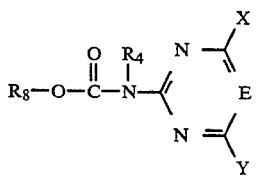
(III)

in which X, Y, $R_4$ and E are as defined under formula I in claim 1 and $R_8$ is $C_1$-$C_4$alkyl, or phenyl which can be substituted by $C_1$-$C_4$alkyl or halogen, in the presence of a base, or b) a pyridylsulfonamide of the formula XII

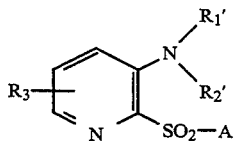
(XII)

in which $R_1'$, $R_2'$ are as defined under $R_1$ and $R_2$ in formula I in claim 1, with the exception of hydrogen, $R_3$ is as defined under formula I in claim 1, and A is

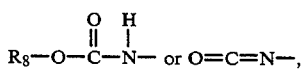

$R_8$ being as defined above, with a 2-aminopyrimidine or -triazine of the formula XI

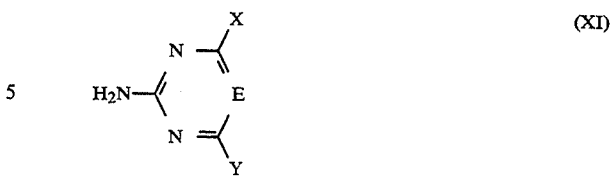
(XI)

in which E, X and Y are as defined under formula I, in the presence of a base.

Compounds of the formula Ia

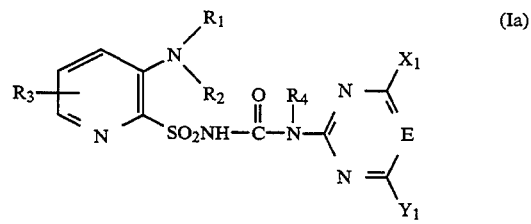
(Ia)

in which $R_1$, $R_2$, $R_3$, $R_4$ and E are as defined under formula I and $X_1$ and $Y_1$ independently of one another are chlorine or difluoromethoxy, can be prepared by reacting a pyridylsulfonamide of the formula II

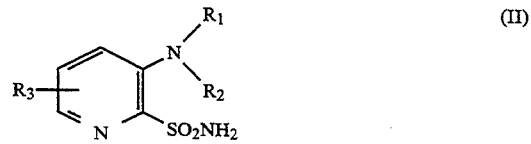
(II)

in which $R_1$, $R_2$ and $R_3$ are as defined under formula I in claim 1, with a pyrimidinyl or triazinyl isocyanate of the formula IV

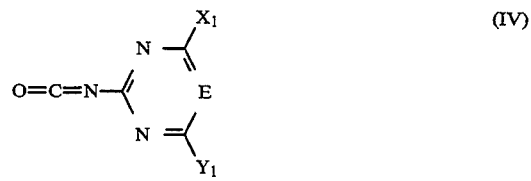
(IV)

in which $X_1$ and $Y_1$ are as defined under formula Ia and E is as defined under formula I, in the presence of a base.

The reactions to give compounds of the formula I are advantageously carried out in aprotic, inert organic solvents. Such solvents are hydrocarbons such as benzene, toluene, xylene or cyclohexane, chlorinated hydrocarbons such as dichloromethane, trichloromethane, tetrachloromethane or chlorobenzene, ethers such as diethyl ether, ethylene glycol dimethyl ether, diethylene glycol dimethyl ether, tetrahydrofuran or dioxane, nitriles such as acetonitrile or propionitrile and amides such as dimethylformamide, diethylformamide or N-methylpyrrolidinone. The reaction temperatures are preferably between −20° and +120° C.

In general, the reactions proceed slightly exothermically and can be carried out at room temperature. To shorten the reaction time, or, alternatively, to initiate the reaction, it is expedient to heat the reaction mixture briefly to boiling point. It is equally possible to shorten the reaction times by adding a few drops of base as a reaction catalyst. Suitable bases are, in particular, tertiary amines such as trimethylamine, triethylamine, quinuclidine, 1,4-diazabicyclo[2.2.2]-octane, 1,5-diazabicyclo[4.3.0]non-5-ene or 1,5-diazabicyclo[5.4.-0]undec-7-ene. Alternatively, inorganic bases, such as hydrides, such as sodium hydride or calcium hydride, hydroxides such as sodium hydroxide and potassium hydroxide, carbonates such as sodium carbonate and potassium carbonate, or hydrogen carbonates such as potassium hydrogen carbonate and sodium hydrogen carbonate, can also be used as bases.

The end products of the formula I can be isolated by concentration and/or by evaporation of the solvent and purified by recrystallisation or trituration of the solid residue in solvents in which they are not readily soluble, such as ethers, aromatic hydrocarbons or chlorinated hydrocarbons.

The intermediates of the formulae XII, III and IV are known or can be prepared analogously to known processes. Processes for the preparation of N-pyrimidinyl- and N-triazinylcarbamates are described, for example, in EP-A 0 101 670. N-Pyrimidinyl and N-triazinyl isocyanates can be prepared from the corresponding 2-aminopyrimidines or -triazines of the formula XI. Reactions of this type as well as the preparation of the compounds of the formula XII are described in EP-A 0 044 808. Compounds of the formula XI are disclosed in EP-A 0 070 804. With the exception of the compound in which $R_1$, $R_2$ and $R_3$ are hydrogen, the intermediates of the formula II are novel and were developed specifically for synthesising the compounds of the formula I. They form therefore a part of the present invention.

The novel intermediates of the formula II can be prepared by various methods which are known per se. For example, the compounds of the formula II are obtained by reacting a 3-halopyridin-2-ylsulfonamide of the formula V

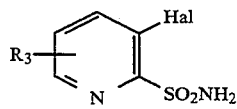 (V)

in which $R_3$ is as defined under formula I and Hal is fluorine or chlorine, with an amine of the formula VI

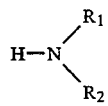 (VI)

in which $R_1$ and $R_2$ are as defined under formula I, in the presence of a base. Preferred compounds for these reactions are those compounds of the formula V in which Hal is fluorine. Syntheses of this type are described, for example, in EP-A 103 543.

Alternatively, the compounds of the formula II can be prepared by reacting a 3-aminopyridin-2-ylsulfonamide of the formula VII

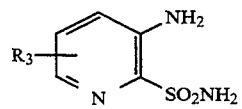 (VII)

in which $R_3$ is as defined under formula I, with a compound of the formula VIII $$Z-R_1 \quad (VIII)$$

in which $R_1$ is as defined under formula I and Z is bromine, iodine,

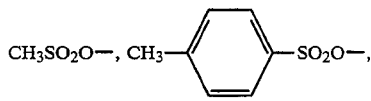

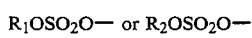

in the presence of a base, to give the compound of the formula IX

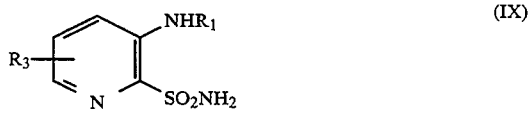 (IX)

in which $R_3$ is as defined under formula I, and subsequently reacting this compound with a compound of the formula X $$Z-R_2 \quad (X)$$

in which $R_2$ is as defined under formula I and Z is as defined under formula VIII, in the presence of a base, to give the compound of the formula II. Reactions of this type are described, for example in Farmaco Ed. scient. 12, 392 (1957). The sulfonamide intermediates of the formulae V and VII are known. They can be prepared, for example, analogously to J. Pharm. Belg. 39, 217–224 (1984).

As a rule, the active substances of the formula I are sucessfully employed at application rates from 0.001 to 2 kg/ha, in particular 0.005 to 1 kg/ha. The dosage rate which is required for the desired action can be determined by tests. It depends on the nature of the action, the development stage of the crop plant and the weed, as well as on the application (location, time, method) and, due to these parameters, can vary within wide limits.

Used at low application rates, the compounds of the formula I are distinguished by growth-inhibiting and herbicidal properties, which make them outstandingly suitable for use in crops of useful plants, in particular in cereals, cotton, soybeans, oilseed rape, corn and rice, the use in corn crops being very particularly preferred.

The invention also relates to herbicidal and plant-growth-regulating compositions which comprise a novel active substance of the formula I, as well as methods for inhibiting plant growth.

Plant growth regulators are substances which cause agronomically desirable biochemical and/or physiological and/or morphological modifications in/on the plant.

The active substances contained in the compositions according to the invention affect plant growth in many ways, depending on the point in time of application, the dosage rate, the type of application and the prevailing environment. For example, plant growth regulators of the formula I can inhibit the vegetative growth of plants. This type of action is of interest on lawns, in the production of ornamental, in orchards, on verges, on sports grounds and industrial terrain, but also in the targeted inhibition of secondary shoots, such as in tobacco. In arable farming, inhibition of the vegetative growth in cereals by strengthening the stem results in reduced lodging, and similar agronomical effects are achieved in oilseed rape, sunflowers, maize and other crop plants. Furthermore, inhibition of the vegetative growth means that the number of plants per unit area can be increased. Another field in which growth inhibitors can be applied is the selective control of groundcover plants, in plantations or crops with plenty of space between the rows, by powerful growth inhibition without destroying these cover crops, so that competition with the main crop is eliminated, but the agronomically positive effects, such as reduction of erosion, nitrogen fixation and loosening of the soil, are retained.

A method for inhibiting plant growth is understood as meaning controlling the natural development of the plant without altering the life cycle of the plant, which is determined by its genetic make-up, in the sense of a mutation. The method of growth regulation is applied at a particular point in time of the development of the plant, which is to be determined in the particular case. The active substances of the formula I can be applied before or after emergence of the plants, for example already to the seeds or seedlings, to roots, tubers, stalks, leaves, flowers or other parts of the plants. This can be effected, for example, by applying the active substance, as such or in the form of a composition, to the plants and/or by treating the nutrient substrate of the plant (soil).

Various methods and techniques are suitable for using the compound of the formula I or compositions containing it for regulating plant growth, for example the following:

i) Seed treatment a) The seeds are treated with an active substance formulated as a wettable powder by shaking in a container until the seed surface is uniformly covered (dry seed treatment). Up to 4 g of active substance of the formula I are used per kg of seed in this method (up to 8.0 g of wettable powder in the case of a 50% formulation).

b) Treating the seeds with an emulsion concentrate of the active substance or with an aqueous solution of the active substance of the formula I formulated as a wettable powder, using method a) (wet seed treatment).

c) Seed treatment by immersing the seeds in a liquor containing up to 1000 ppm of active substance of the formula I for 1 to 72 hours, which, if desired, is followed by drying the seeds (seed soaking).

Naturally, seed treatment or treatment of the germinated seedling are the preferred application methods since the treatment with active substance is directed entirely at the target crop. 0.001 g to 4.0 g of active compound are generally used per kg of seed, but it is possible to deviate from the limit concentrations given in both directions, depending on the method chosen which also makes possible the addition of other active substances or micronutrients (repeated seed treatment).

ii) Controlled release of active substance

The dissolved active substance is applied to mineral granule carriers or polymerised granules (urea/formaldehyde) and allowed to dry. If desired, a coating can be applied (coated granules), which permits slow release of the active substance over a certain period.

The compounds of the formula I are employed in unaltered form, as obtainable by the synthesis, or preferably together with the auxiliaries conventionally used in formulation technology, and they are therefore processed in a known manner to give, for example, emulsifiable concentrates, directly sprayable or dilutable solutions, dilute emulsions, wettable powders, soluble powders, dusts, granules, and also encapsulations, for example in polymeric substances. The application methods, such as spraying, atomising, dusting, scattering or pouring, as well as the type of compositions are selected to suit the intended aims and the prevailing circumstances.

The formulations, i.e. the compositions, preparations or combinations comprising the active substance of the formula I and, if desired, one or more solid or liquid additives, are prepared in a known manner, for example by intimately mixing and/or grinding the active substances with extenders, for example with solvents, solid carriers and, if desired, surface-active compounds (surfactants).

The following are possible as solvents: aromatic hydrocarbons, in particular the fractions $C_8$ to $C_{12}$, such as mixtures of alkylbenzenes, for example xylene mixtures or alkylated naphthalenes; aliphatic and cycloaliphatic hydrocarbons such as paraffins, cyclohexane or tetrahydronaphthalene; alcohols, such as ethanol, propanol or butanol; glycols as well as their ethers and esters, such as propylene glycol or dipropylene glycol ether, ketones such as cyclohexanone, isophorone or diacetone alcohol, strongly polar solvents such as N-methyl-2-pyrrolidone, dimethyl sulfoxide or water; vegetable oils as well as their esters, such as rapeseed oil, castor oil or soybean oil; and if appropriate also silicone oils.

Solid carriers which are generally used, for example for dusts and dispersible powders, are ground natural minerals, such as calcite, talc, kaolin, montmorillonite or attapulgite. To improve the physical properties, it is also possible to add highly-disperse silica or highly-disperse absorptive polymers. Possible particulate, adsorptive carriers for granules are either porous types, for example pumice, brick grit, sepiolite or bentonite, or non-sorptive carrier materials, such as calcite or sand. Moreover, a large number of pregranulated materials of inorganic or organic nature can be used, such as, in particular, dolomite or comminuted plant residues.

Suitable surface-active compounds are non-ionic, cationic and/or anionic surfactants having good emulsifying, dispersing and wetting properties, depending on the nature of the active substance of the formula I to be formulated. Surfactants are also to be understood as meaning mixtures of surfactants.

Anionic surfactants which are suitable can be either so-called water-soluble soaps or water-soluble synthetic surface-active compounds. Suitable soaps which may be mentioned are the alkali metal salts, alkaline earth metal salts or substituted or unsubstituted ammonium salts of higher fatty acids ($C_{10}$–$C_{22}$), such as the Na salts or K salts of oleic or stearic acid, or of natural mixtures of fatty acids which can be obtained, for example, from coconut oil or tallow oil. Mention must also be made of the fatty acid methyltaurinates.

However, so-called synthetic surfactants are used more frequently, in particular fatty alcohol sulfonates, fatty alcohol sulfates, sulfonated benzimidazole derivatives or alkylarylsulfonates.

The fatty alcohol sulfonates or fatty alcohol sulfates are generally in the form of alkali metal salts, alkaline earth metal salts or substituted or unsubstituted ammonium salts, and have an alkyl radical having 8 to 22 C atoms, alkyl also including the alkyl moiety of acyl radicals, for example the Na or Ca salt of ligninsulfonic acid, of the dodecylsulfuric ester or of a fatty alcohol sulfate mixture prepared from natural fatty acids. This group also includes the salts of the sulfuric esters and sulfonic acids of fatty alcohol/ethylene oxide adducts. The sulfonated benzimidazole derivatives preferably contain 2 sulfonyl groups and one fatty acid radical having 8 to 22 C atoms. Examples of alkylarylsulfonates are the Na, Ca or triethanolamine salts of dodecylbenzenesulfonic acid, of dibutylnaphthalenesulfonic acid or of a naphthalenesulfonic acid/formaldehyde condensation product.

Other suitable compounds are the corresponding phosphates, such as the salts of the phosphoric ester of a p-nonylphenol/(4–14)-ethylene oxide adduct, or phospholipids.

Suitable non-ionic surfactants are mainly polyglycol ether derivatives of aliphatic or cycloaliphatic alcohols, of saturated or unsaturated fatty acids and of alkylphenols, which can contain 3 to 30 glycol ether groups and 8 to 20 carbon atoms in the (aliphatic) hydrocarbon radical and 6 to 18 carbon atoms in the alkyl radical of the alkylphenols.

Other non-ionic surfactants which are suitable are the water-soluble polyethylene oxide adducts with polypropylene glycol, ethylenediaminopolypropylene glycol and alkylpolypropylene glycol which have 1 to 10 carbon atoms in the alkyl chain and which contain 20 to 250 ethylene glycol ether groups and 10 to 100 propylene glycol ether groups. The abovementioned compounds customarily contain 1 to 5 ethylene glycol units per propylene glycol unit. Examples of non-ionic surfactants which may be mentioned are nonylphenolpolyethoxyethanols, castor oil polyglycol ethers, polypropylene/polyethylene oxide adducts, tributylphenoxypolyethoxyethanol, polyethylene glycol and octylphenoxypolyethoxyethanol.

Other suitable substances are fatty acid esters of polyoxyethylenesorbitan, such as polyoxyethylenesorbitan trioleate.

The cationic surfactants are mainly quaternary ammonium salts, which contain at least one alkyl radical having 8 to 22 C atoms as N-substituents and which have lower halogenated or free alkyl, benzyl or lower hydroxyalkyl radicals as further substituents. The salts are preferably in the form of halides, methylsulfates or ethylsulfates, for example stearyltrimethylammonium chloride or benzyldi(2-chloroethyl)ethylammonium bromide.

The surfactants customary in formulation technology are described, inter alia, in the following publications:
"McCutcheon's Detergents and Emulsifiers Annual", Mc Publishing Corp., Glen Rock, N.J., 1988;

M. and J. Ash. "Encyclopedia of Surfactants", Vol. I–III, Chemical Publishing Co., New York, 1980–1981.

Dr. Helmut Stache, "Tensid-Taschenbuch [Surfactant Guide]", Carl Hanser Verlag, Munich, Vienna, 1981;

As a rule, the pesticidal preparations contain 0.1 to 99%, in particular 0.1 to 95%, of the active substance of the formula I, 1 to 99% of a solid or liquid additive and 0 to 25%, in particular 0.1 to 25%, of a surfactant.

While concentrated compositions are more preferred as commercial goods, the user generally uses dilute compositions.

The compositions can also comprise further additives such as stabilisers, for example epoxidised or unepoxidised vegetable oils (epoxidised coconut oil, repeseed oil or soybean oil), defoamers, for example silicone oil, preservatives, viscosity regulators, binders, tackifiers, as well as fertilisers or other active substances for achieving specific effects.

In particular, preferred formulations have the following composition: (%=percent by weight)

| Emulsifiable concentrates: | |
| --- | --- |
| Active ingredient: | 1 to 90%, preferably 5 to 20% |
| Surface-active agent: | 1 to 30%, preferably 10 to 20% |
| Liquid carrier: | 50 to 94%, preferably 70 to 85% |
| Dusts: | |
| Active ingredient: | 0.1 to 10%, preferably 0.1 to 1% |
| Solid carrier: | 99.9 to 90%, preferably 99.9 to 99% |
| Suspension concentrates: | |
| Active ingredient: | 5 to 75%, preferably 10 to 50% |
| Water: | 94 to 24%, preferably 88 to 30% |
| Surface-active agent: | 1 to 40%, preferably 2 to 30% |
| Wettable powders: | |
| Active ingredient: | 0.5 to 90%, preferably 1 to 80% |
| Surface-active agent: | 0.5 to 20%, preferably 1 to 15% |
| Solid carrier material: | 5 to 95%, preferably 15 to 90%. |
| Granules: | |
| Active ingredient: | 0.5 to 30%, preferably 3 to 15% |
| Solid carrier material: | 99.5 to 70%, preferably 97 to 85%. |

PREPARATION EXAMPLES

EXAMPLE H1

Preparation of N-(3-n-butylaminopyridin-2-ylsulfonyl)-N'-(4,6-dimethoxypyrimidin-2-yl)urea (compound No. 1.001)

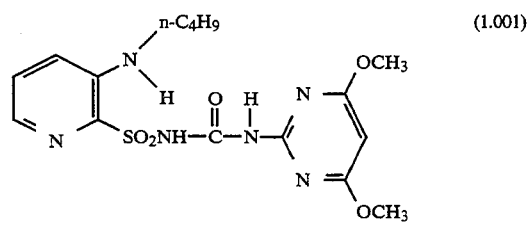

(1.001)

The following are added in succession to a mixture of 2.75 g of 3-n-butylaminopyridin-2-ysulfonamide in 40 ml of acetonitrile: 3.5 g of phenyl N-(4,6-dimethoxypyrimidin-2-yl)carbamate and 1.97 ml of 1,5-diazabicyclo[5.4.0]undec-5-ene. The reaction mixture is stirred for 30 minutes and evaporated, the oily residue is triturated with 10 ml of 2N hydrochloric acid and subsequently with 10 ml of ice/water and a little diethyl ether, and the mixture is filtered. The filter residue is subsequently washed with a little water and diethyl ether and dried. 4.39 g of N-(3-n-butylaminopyridin-2-ylsulfonyl)-N'-(4,6-dimethoxypyrimidin-2-yl)urea (compound No. 1.001) of a melting point of 118°–119° C. are obtained.

EXAMPLE H2

Preparation of 3-n-butylaminopyridin-2-ylsulfonamide (intermediate No. 2.001)

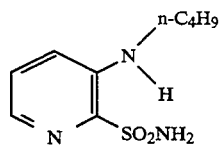

49.6 ml of n-butylamine are added to a mixture of 8.81 g of 3-fluoropyridin-2-ylsulfonamide in 10 ml of tetrahydrofuran (THF). After the reaction mixture has been stirred for 18 hours at a temperature of 60° C., the reaction mixture is evaporated, the oily residue is triturated with 100 ml of ice/water, the mixture is filtered, and the filtrate is washed first with a little cold water and subsequently with n-hexane. After drying at a temperature of 45° C. in vacuo, 8.8 g of 3-n-butylaminopyridin-2-ylsulfonamide (intermediate No. 2.001) of a melting point of 100°–101° C. are obtained.

EXAMPLE H3

Allylaminopyridin-2-ylsulfonamide (intermediate No. 2.002)

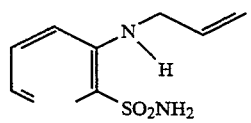

5.28 g of 3-fluoropyridin-2-ylsulfonamide and 18.03 ml of allylamine are stirred for 6 hours in a pressurised vessel at a temperature of 125° C. The reaction solution is subsequently concentrated, the crystallisate obtained is dissolved in methylene chloride and a little acetonitrile, the mixture is purified by chromatography using methylene chloride/ethyl acetate (4:1) as the eluent mixture and silica gel as the carrier material. 5.1 g of 3-allylaminopyridin-2-ylsulfonamide (intermediate No. 2.002) of a melting point of 134°–135° C. are obtained.

The compounds of the formula I as well as the intermediates of the formula II which are listed in the appended tables are prepared analogously.

TABLE 1

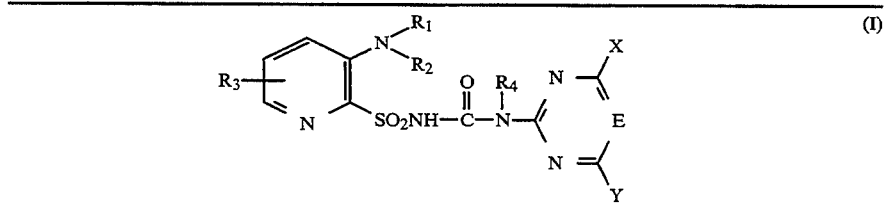

| No. | $R_1$ | $R_2$ | $R_3$ | $R_4$ | X | Y | E | M.p. [°C.] |
|---|---|---|---|---|---|---|---|---|
| 1.001 | n-$C_4H_9$ | H | H | H | $CH_3O$ | $CH_3O$ | CH | 118–119 |
| 1.002 | n-$C_4H_9$ | H | H | H | $CH_3O$ | Cl | CH | |
| 1.003 | n-$C_4H_9$ | H | H | H | $CH_3O$ | $CH_3$ | CH | |
| 1.004 | n-$C_4H_9$ | H | H | H | $CH_3O$ | $CH_3$ | N | |
| 1.005 | n-$C_4H_9$ | H | H | H | $CH_3O$ | $OCHF_2$ | CH | |
| 1.006 | n-$C_4H_9$ | H | H | H | $CH_3$ | $OCHF_2$ | CH | |
| 1.007 | n-$C_4H_9$ | H | H | H | $CH_3O$ | $OC_2H_5$ | N | |
| 1.008 | H | H | H | H | $CH_3O$ | $CH_3O$ | CH | 132–134 |
| 1.009 | H | H | H | H | $CH_3O$ | Cl | CH | |
| 1.010 | H | H | H | H | $CH_3O$ | $CH_3$ | N | |
| 1.011 | H | H | H | H | $CH_3$ | $OCHF_2$ | CH | |
| 1.012 | $CH_3$ | H | H | H | $OCH_3$ | Cl | CH | 167–169 |
| 1.013 | $CH_3$ | H | H | H | $OCH_3$ | $OCH_3$ | CH | 147–148 |
| 1.014 | $CH_3$ | H | H | H | $OCH_3$ | $CH_3$ | N | 141–143 |
| 1.015 | $CH_3$ | H | H | H | $OCH_3$ | $OCHF_2$ | CH | |
| 1.016 | $CH_3$ | H | H | H | $OCHF_2$ | $OCHF_2$ | CH | |
| 1.017 | $CH_3$ | $CH_3$ | H | H | $OCH_3$ | $OCH_3$ | CH | 134–135 |
| 1.018 | $CH_3$ | H | H | H | $OCH_3$ | Cl | CH | 128–130 |
| 1.019 | $CH_3$ | H | H | H | $OCH_3$ | $CH_3$ | N | 178–181 |
| 1.020 | $CH_3$ | H | H | H | $OCH_3$ | $OCHF_2$ | CH | |
| 1.021 | $CH_3$ | H | H | H | $CH_3$ | $OC_2H_5$ | N | |
| 1.022 | $CH_3$ | H | H | H | $OCHF_2$ | $OCHF_2$ | CH | |
| 1.023 | $C_2H_5$ | H | H | H | $OCH_3$ | $OCH_3$ | CH | 140–141 |
| 1.024 | $C_2H_5$ | H | H | H | $OCH_3$ | $CH_3$ | N | |
| 1.025 | $C_2H_5$ | H | H | H | $OCHF_2$ | $OCHF_2$ | CH | |
| 1.026 | $C_2H_5$ | H | H | H | $OCH_3$ | Cl | CH | |
| 1.027 | —$CH(CH_3)_2$ | H | H | H | $OCH_3$ | $OCH_3$ | CH | 134–135 |
| 1.028 | —$CH(CH_3)_2$ | H | H | H | $OCH_3$ | Cl | CH | 118–121 |
| 1.029 | —$CH(CH_3)_2$ | H | H | H | $OCHF_2$ | $OCHF_2$ | CH | |
| 1.030 | —$CH(CH_3)_2$ | H | H | H | $OCH_3$ | $CH_3$ | N | 131–133 |
| 1.031 | —$CH(CH_3)_2$ | H | H | H | $OC_2H_5$ | $CH_3$ | N | |
| 1.032 | —$C_2H_5$ | $CH_3$ | H | H | $OCH_3$ | $OCH_3$ | CH | 124–126 |
| 1.033 | —$C_2H_5$ | $CH_3$ | H | H | $OCH_3$ | Cl | CH | |
| 1.034 | —$C_2H_5$ | $CH_3$ | H | H | $OCHF_2$ | $OCHF_2$ | CH | |
| 1.035 | —$C_2H_5$ | $CH_3$ | H | H | $OCH_3$ | $CH_3$ | N | |
| 1.036 | —$C_2H_5$ | $CH_3$ | H | H | $OC_2H_5$ | $CH_3$ | N | |
| 1.037 | —$CH(CH_3)_2$ | $CH_3$ | H | H | $OCH_3$ | $OCH_3$ | CH | 135–136 |
| 1.038 | —$CH(CH_3)_2$ | $CH_3$ | H | H | $OCH_3$ | Cl | CH | |
| 1.039 | —$CH(CH_3)_2$ | $CH_3$ | H | H | $OCH_3$ | $CH_3$ | N | |
| 1.040 | —$CH(CH_3)_2$ | $CH_3$ | H | H | $OC_2H_5$ | $CH_3$ | N | |
| 1.041 | —$CH(CH_3)_2$ | $CH_3$ | H | H | $OCHF_2$ | $OCHF_2$ | CH | |

TABLE 1-continued (I)

$$R_3 \text{—pyridine—N}(R_1)(R_2),\ \text{—SO}_2\text{NH—C(=O)—N}(R_4)\text{—[triazine/pyrimidine with X, Y, E]}$$

| No. | $R_1$ | $R_2$ | $R_3$ | $R_4$ | X | Y | E | M.p. [°C] |
|---|---|---|---|---|---|---|---|---|
| 1.042 | $C_4H_9$-(n) | $CH_3$ | H | H | $OCHF_2$ | $OCHF_2$ | CH | |
| 1.043 | $C_4H_9$-(n) | $CH_3$ | H | H | $OCH_3$ | $OCH_3$ | CH | 126–127 |
| 1.044 | $C_4H_9$-(n) | $CH_3$ | H | H | $OCH_3$ | $OCH_3$ | N | |
| 1.045 | $C_4H_9$-(n) | $CH_3$ | H | H | $OCH_3$ | $CH_3$ | N | |
| 1.046 | $C_4H_9$-(n) | $CH_3$ | H | H | $OC_2H_5$ | $CH_3$ | N | |
| 1.047 | $C_4H_9$-(n) | $CH_3$ | H | H | $OCH_3$ | Cl | CH | |
| 1.048 | $CH_2$=$CHCH_2$ | H | H | H | $OCH_3$ | $OCH_3$ | CH | 130–133 |
| 1.049 | $CH_2$=$CHCH_2$ | H | H | H | $OCH_3$ | Cl | CH | |
| 1.050 | $CH_2$=$CHCH_2$ | H | H | H | $OCH_3$ | $OCH_3$ | CH | |
| 1.051 | $CH_2$=$CHCH_2$ | H | H | H | $OCH_3$ | $CH_3$ | N | 110–113 |
| 1.052 | $CH_2$=$CHCH_2$ | H | H | H | $OC_2H_5$ | $CH_3$ | N | |
| 1.053 | $CH_2$=$CHCH_2$ | H | H | H | $OCHF_2$ | $OCHF_2$ | CH | |
| 1.054 | $CH_2$=$CHCH_2$ | $CH_2$=$CHCH_2$ | H | H | $OCHF_2$ | $OCHF_2$ | CH | |
| 1.055 | $CH_2$=$CHCH_2$ | $CH_2$=$CHCH_2$ | H | H | $OCH_3$ | $OCHF_2$ | CH | |
| 1.056 | $CH_2$=$CHCH_2$ | $CH_2$=$CHCH_2$ | H | H | $OCH_3$ | $OCH_3$ | CH | 136–138 |
| 1.057 | $CH_2$=$CHCH_2$ | $CH_2$=$CHCH_2$ | H | H | $OCH_3$ | $CH_3$ | N | |
| 1.058 | $CH_2$=$CHCH_2$ | $CH_2$=$CHCH_2$ | H | H | $OC_2H_5$ | $CH_3$ | N | |
| 1.059 | $CH_2$=$CHCH_2$ | $CH_2$=$CHCH_2$ | H | H | $OCH_3$ | Cl | CH | |
| 1.060 | HC≡$CCH_2$ | H | H | H | $OCH_3$ | Cl | CH | |
| 1.061 | HC≡$CCH_2$ | H | H | H | $OCH_3$ | $OCH_3$ | CH | 155–157 |
| 1.062 | HC≡$CCH_2$ | H | H | H | $OCHF_2$ | $OCHF_2$ | CH | |
| 1.063 | HC≡$CCH_2$ | H | H | H | $OCH_3$ | $CH_3$ | N | |
| 1.064 | HC≡$CCH_2$ | H | H | H | $OC_2H_5$ | $CH_3$ | N | 132–134 |
| 1.065 | H | H | 6-$CH_3$ | H | $OCH_3$ | $CH_3$ | N | |
| 1.066 | H | H | H | H | $OCH_3$ | Cl | CH | |
| 1.067 | H | H | H | H | $OCH_3$ | $OCH_3$ | CH | |
| 1.068 | $CH_3$ | H | H | H | $OCH_3$ | $OCH_3$ | CH | |
| 1.069 | $CH_3$ | H | H | H | $OCH_3$ | $CH_3$ | N | |
| 1.070 | $CH_3$ | $CH_3$ | H | H | $OCH_3$ | $CH_3$ | N | |
| 1.071 | $CH_3$ | $CH_3$ | H | H | $OCH_3$ | Cl | CH | |
| 1.072 | $C_2H_5$ | H | H | H | $OCH_3$ | Cl | CH | |
| 1.073 | $C_2H_5$ | H | H | H | $OCH_3$ | $CH_3$ | N | |
| 1.074 | —$CH(CH_3)_2$ | $CH_3$ | H | H | $OCH_3$ | $CH_3$ | N | |
| 1.075 | —$CH(CH_3)_2$ | $CH_3$ | H | H | $OCH_3$ | $OCH_3$ | CH | |
| 1.076 | —$CH(CH_3)_2$ | $CH_3$ | H | H | $OCH_3$ | Cl | CH | |
| 1.077 | $CH_3$ | $CH_3$ | H | H | $CH_3$ | $OCH_3$ | CH | 126–128 |
| 1.078 | —$(CH_2)_5$— | | H | H | $CH_3$ | $OCH_3$ | N | 138–140 |
| 1.079 | —$(CH_2)_5$— | | H | H | $OCH_3$ | $OCH_3$ | CH | 126–130 |
| 1.080 | —$(CH_2)_5$— | | H | H | $OCH_3$ | $CH_3$ | CH | |
| 1.081 | —$(CH_2)_5$— | | H | H | $CH_3$ | $CH_3$ | CH | |
| 1.082 | —$(CH_2)_2$—N($CH_3$)—$(CH_2)_2$— | | H | H | $CH_3$ | $CH_3$ | N | 166–168 |
| 1.083 | —$(CH_2)_2$—N($CH_3$)—$(CH_2)_2$— | | H | H | $OCH_3$ | $OCH_3$ | CH | |
| 1.084 | —$(CH_2)_2$—O—$(CH_2)_2$— | | H | H | $OCH_3$ | $CH_3$ | N | 148–150 |
| 1.085 | —$(CH_2)_2$—O—$(CH_2)_2$— | | H | H | $OCH_3$ | $CH_3$ | CH | |
| 1.086 | —$(CH_2)_2$—O—$(CH_2)_2$— | | H | H | $OCH_3$ | $OCH_3$ | CH | 156–159 |
| 1.087 | —$CH_2CH(CH_3)_2$ | H | H | H | $OCH_3$ | $CH_3$ | N | 131–133 |
| 1.088 | —$CH_2CH(CH_3)_2$ | H | H | H | $OCH_3$ | $CH_3$ | CH | |
| 1.089 | —$CH_2CH(CH_3)_2$ | H | H | H | $OCH_3$ | $OCH_3$ | CH | 110–114 |
| 1.090 | —$C_6H_{13}$(n) | H | H | H | $OCH_3$ | $OCH_3$ | CH | 112–114 |
| 1.091 | —$C_6H_{13}$(n) | H | H | H | $OCH_3$ | $CH_3$ | CH | |
| 1.092 | —$C_6H_{13}$(n) | H | H | H | $OCH_3$ | $CH_3$ | N | 100–102 |
| 1.093 | —$CH_2CH(CH_3)_2$ | H | H | H | $OCH_3$ | Cl | CH | 108–109 |
| 1.094 | —$CH(CH_3)_2$ | H | H | H | $CH_3$ | $OCHF_2$ | CH | 70–72 |
| 1.095 | —$CH(CH_3)_2$ | H | H | H | $CH_3$ | $OCH_3$ | CH | 145–147 |
| 1.096 | $CH_3$ | $CH_3$ | H | H | $CH_3$ | $CH_3$ | CH | 132–135 |
| 1.097 | HC≡$CCH_2$ | H | H | H | $CH_3$ | $OCH_3$ | CH | 157–159 |
| 1.098 | HC≡$CCH_2$ | H | H | H | $CH_3$ | $CH_3$ | CH | 150–151 |
| 1.099 | $CH_3$ | $CH_3$ | 6-$CH_3$ | H | $OCH_3$ | $OCH_3$ | CH | |
| 1.100 | $CH_3$ | $CH_3$ | 6-$CH_3$ | H | $CH_3$ | $OCH_3$ | CH | |
| 1.101 | $CH_3$ | $CH_3$ | 6-$CH_3$ | H | Cl | $OCH_3$ | CH | |
| 1.102 | $CH_3$ | $CH_3$ | 6-$CH_3$ | H | $OCHF_2$ | $OCH_3$ | CH | |
| 1.103 | $CH_3$ | $CH_3$ | 6-$CH_3$ | H | $OCH_3$ | $OCH_3$ | N | |
| 1.104 | $CH_3$ | H | 6-$CH_3$ | H | $OCH_3$ | $OCH_3$ | CH | |
| 1.105 | $CH_3$ | H | 6-$CH_3$ | H | $CH_3$ | $OCH_3$ | CH | |

TABLE 1-continued

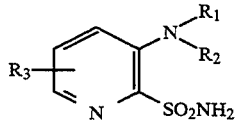

(I)

| No. | R₁ | R₂ | R₃ | R₄ | X | Y | E | M.p. [°C.] |
|---|---|---|---|---|---|---|---|---|
| 1.106 | CH₃ | H | 6-CH₃ | H | Cl | OCH₃ | CH | |
| 1.107 | CH₃ | H | 6-CH₃ | CH₃ | OCH₃ | OCH₃ | CH | |
| 1.108 | C₂H₅ | CH₃ | 6-CH₃ | H | OCH₃ | OCH₃ | CH | |
| 1.109 | C₂H₅ | CH₃ | 6-CH₃ | H | CH₃ | OCH₃ | CH | |
| 1.110 | C₂H₅ | CH₃ | 6-CH₃ | H | CH₃ | CH₃ | CH | |
| 1.111 | C₂H₅ | H | 6-CH₃ | H | OCH₃ | OCH₃ | CH | |
| 1.112 | C₂H₅ | H | 6-CH₃ | H | OCH₃ | OCH₃ | N | |
| 1.113 | C₂H₅ | H | 6-CH₃ | H | CH₃ | OCH₃ | CH | |
| 1.114 | CH₃ | CH₃ | 5-CH₃ | H | OCH₃ | OCH₃ | CH | |
| 1.115 | CH₃ | CH₃ | 5-CH₃ | H | CH₃ | OCH₃ | CH | |
| 1.116 | CH₃ | H | 5-CH₃ | H | OCH₃ | OCH₃ | CH | |
| 1.117 | C₂H₅ | H | 5-CH₃ | H | OCH₃ | OCH₃ | CH | |
| 1.118 | C₂H₅ | CH₃ | 5-CH₃ | H | OCH₃ | OCH₃ | CH | |
| 1.119 | CH₃ | CH₃ | 4-CH₃ | H | OCH₃ | OCH₃ | CH | |
| 1.120 | CH₃ | H | 4-CH₃ | H | OCH₃ | OCH₃ | CH | |
| 1.121 | C₂H₅ | H | 4-CH₃ | H | OCH₃ | OCH₃ | CH | |
| 1.122 | C₂H₅ | CH₃ | 4-CH₃ | H | OCH₃ | OCH₃ | CH | |
| 1.123 | CH₃ | CH₃ | 6-OCH₃ | H | OCH₃ | OCH₃ | CH | |
| 1.124 | CH₃ | CH₃ | 6-OCH₃ | H | OCH₃ | CH₃ | CH | |
| 1.125 | CH₃ | CH₃ | 6-OCH₃ | H | Cl | OCH₃ | CH | |
| 1.126 | CH₃ | CH₃ | 6-OCH₃ | H | OCHF₂ | OCHF₂ | CH | |
| 1.127 | CH₃ | CH₃ | 6-OCH₃ | H | CH₃ | OCH₃ | N | |
| 1.128 | CH₃ | H | 6-OCH₃ | H | OCH₃ | OCH₃ | CH | |
| 1.129 | CH₃ | H | 6-OCH₃ | H | CH₃ | OCH₃ | CH | |
| 1.130 | CH₃ | H | 6-OCH₃ | H | Cl | OCH₃ | CH | |
| 1.131 | CH₃ | H | 6-OCH₃ | CH₃ | OCH₃ | OCH₃ | CH | |
| 1.132 | C₂H₅ | CH₃ | 6-OCH₃ | H | OCH₃ | OCH₃ | CH | |
| 1.133 | C₂H₅ | CH₃ | 6-OCH₃ | H | CH₃ | OCH₃ | CH | |
| 1.134 | C₂H₅ | CH₃ | 6-OCH₃ | H | CH₃ | CH₃ | CH | |
| 1.135 | C₂H₅ | H | 6-OCH₃ | H | OCH₃ | OCH₃ | CH | |
| 1.136 | C₂H₅ | H | 6-OCH₃ | H | OCH₃ | OCH₃ | N | |
| 1.137 | C₂H₅ | H | 6-OCH₃ | H | CH₃ | OCH₃ | CH | |
| 1.138 | CH₃ | CH₃ | 6-OCHF₂ | H | OCH₃ | OCH₃ | CH | |
| 1.139 | CH₃ | H | 6-OCHF₂ | H | OCH₃ | OCH₃ | CH | |
| 1.140 | C₂H₅ | CH₃ | 6-OCHF₂ | H | OCH₃ | OCH₃ | CH | |
| 1.141 | CH₃ | CH₃ | 5-Cl | H | OCH₃ | OCH₃ | CH | |
| 1.142 | CH₃ | CH₃ | 5-Cl | H | CH₃ | OCH₃ | CH | |
| 1.143 | CH₃ | H | 5-Cl | H | OCH₃ | OCH₃ | CH | |
| 1.144 | CH₃ | CH₃ | 5-CF₃ | H | OCH₃ | OCH₃ | CH | |
| 1.145 | CH₃ | H | 4-CF₃ | H | OCH₃ | OCH₃ | CH | |
| 1.146 | CH₃ | CH₃ | 4-CF₃ | H | OCH₃ | OCH₃ | CH | |

TABLE 2

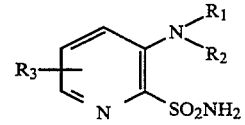

(II)

| No. | R₁ | R₂ | R₃ | M.p. [°C.] |
|---|---|---|---|---|
| 2.001 | n-C₄H₉ | H | H | 100–101 |
| 2.002 | CH₂=CHCH₂ | H | H | 134–135 |
| 2.003 | H | H | H | 186–188 |
| 2.004 | CH₃ | H | H | 147–148 |
| 2.005 | CH₃ | CH₃ | H | 111–113 |
| 2.006 | C₂H₅ | H | H | 149–150 |
| 2.007 | —CH(CH₃)₂ | H | H | 96–97 |
| 2.008 | C₂H₅ | CH₃ | H | 79–80 |
| 2.009 | —CH(CH₃)₂ | CH₃ | H | 128–130 |
| 2.010 | -(n)-C₄H₉ | CH₃ | H | Oil |
| 2.011 | CH₂=CHCH₂ | CH₂=CHCH₂ | H | 75–76 |
| 2.012 | HC≡C—CH₂ | H | H | 157–158 |
| 2.013 | CH₃ | H | 6-CH₃ | |
| 2.014 | H | H | 6-OCH₃ | |
| 2.015 | CH₃ | H | 6-CH₃ | |
| 2.016 | CH₃ | CH₃ | 6-CH₃ | |
| 2.017 | —CH(CH₃)₂ | H | 6-CH₃ | |
| 2.018 | —CH(CH₃)₂ | CH₃ | 6-CH₃ | |
| 2.019 | CH₃OCH₂CH₂— | H | H | |
| 2.020 | CH₃OCH₂CH₂— | CH₃ | H | |
| 2.021 | (CH₃)₂NCH₂CH₂ | H | H | |
| 2.022 | (CH₃)₂NCH₂CH₂ | CH₃ | H | |
| 2.023 | —(CH₂)₅— | | H | 183–184 |
| 2.024 | —(CH₂)₂—N(CH₃)—(CH₂CH₂)— | | H | 211–212 |
| 2.025 | —(CH₂)₂—O—(CH₂)₂— | | H | 193–194 |
| 2.026 | H | —CH₂CH(CH₃)₂ | H | 107–108 |
| 2.027 | H | —C₆H₁₃(n) | H | 107–108 |
| 2.028 | CH₃ | CH₃ | 6-CH₃ | |

TABLE 2-continued $$R_3 \underset{N}{\overset{}{\diagdown}} \underset{SO_2NH_2}{\overset{N(R_1)(R_2)}{\diagdown}} \quad (II)$$

| No. | R₁ | R₂ | R₃ | M.p. [°C.] |
|---|---|---|---|---|
| 2.029 | CH₃ | H | 6-CH₃ | |
| 2.030 | C₂H₅ | CH₃ | 6-CH₃ | |
| 2.031 | C₂H₅ | H | 6-CH₃ | |
| 2.032 | CH₃ | CH₃ | 6-OCH₃ | |
| 2.033 | CH₃ | H | 6-OCH₃ | |
| 2.034 | C₂H₅ | CH₃ | 6-OCH₃ | |
| 2.035 | C₂H₅ | H | 6-OCH₃ | |
| 2.036 | CH₃ | CH₃ | 5-CH₃ | |
| 2.037 | CH₃ | H | 5-CH₃ | |
| 2.038 | C₂H₅ | CH₃ | 5-CH₃ | |
| 2.039 | C₂H₅ | H | 5-CH₃ | |
| 2.040 | CH₃ | CH₃ | 4-CH₃ | |
| 2.041 | CH₃ | H | 4-CH₃ | |
| 2.042 | C₂H₅ | CH₃ | 4-CH₃ | |
| 2.043 | C₂H₅ | H | 4-CH₃ | |
| 2.044 | CH₃ | CH₃ | 6-OCHF₂ | |
| 2.045 | CH₃ | H | 6-OCHF₂ | |
| 2.046 | C₂H₅ | CH₃ | 6-OCHF₂ | |
| 2.047 | CH₃ | CH₃ | 5-Cl | |
| 2.048 | CH₃ | H | 5-Cl | |
| 2.049 | CH₃ | CH₃ | 5-CF₃ | |
| 2.050 | CH₃ | H | 4-CF₃ | |
| 2.051 | CH₃ | CH₃ | 4-CF₃ | |

BIOLOGICAL EXAMPLES

EXAMPLE B 1

Herbicidal action before emergence of the plants

Plastic pots are filled with expanded vermiculite (density: 0.135 g/cm³, water adsorption capacity: 0.565 l/l). After the non-adsorptive vermiculite has been saturated with an aqueous emulsion of active substance in deionised water, containing the active substances at a concentration of 70.8 ppm, seeds of the following plants are sown on the surface: *Nasturtium officinalis, Agrostis tenuis, Stellaria media* and *Digitaria sanguinalis*. The test containers are subsequently kept in a controlled-environment cabinet at a temperature of 20° C., an illumination of approx. 20 klux and a relative atmospheric humidity of 70%. During a germination phase of 4 to 5 days, the pots are covered with transparent material to increase the local atmospheric humidity, and watered with deionised water. After day 5, 0.5% of a commercially available liquid fertiliser is added to the irrigation water. 12 days after sowing, the test is evaluated, and the action on the test plants is assessed using the following scale:

1: plant not germinated or completely dead
2–3: powerful action
4–6: medium action
7–8: weak action
9: no action (like untreated control)

TABLE B1

Pre-emergence action:
Concentration of the emulsion of active substance: 70.8 ppm

| Active substance No. | Test plant: | | | |
|---|---|---|---|---|
| | Nasturtium | Stellaria | Agrostis | Digitaria |
| 1.001 | 1 | 3 | 1 | 3 |
| 1.008 | 2 | 2 | 2 | 2 |
| 1.012 | 1 | 2 | 1 | 2 |
| 1.013 | 1 | 1 | 1 | 2 |
| 1.014 | 2 | 2 | 2 | 2 |
| 1.017 | 1 | 2 | 1 | 2 |
| 1.018 | 2 | 3 | 2 | 2 |
| 1.019 | 2 | 2 | 1 | 2 |
| 1.023 | 1 | 2 | 1 | 3 |
| 1.027 | 1 | 1 | 1 | 2 |
| 1.043 | 1 | 1 | 1 | 2 |

EXAMPLE B 2

Post-emergence herbicidal action (contact herbicide)

A number of weeds, both monocotyledon and dicotyledon, are sprayed after emergence (in the 4- to 6-leaf stage) with an aqueous dispersion of active substance at a dosage rate of 8–500 g of active substance per hectare, and the plants are kept at 24°–26° C. and 45–60% relative atmospheric humidity.

After 3 weeks, the herbicidal action is assessed using a nine-step key (1=complete damage, 9=no action) in comparison with an untreated control group. Scores from 1 to 4 (in particular 1 to 3) suggest a good to very good herbicidal action. Scores from 6 to 9 (in particular from 7 to 9) suggest a good tolerance (in particular in the case of crop plants).

In this test, the compounds of the formula I show a powerful herbicidal action.

EXAMPLE B 3

Herbicidal action for paddy rice

The aquatic weeds *Echinochloa crus galli* and *Monocharia vag.* are sown in plastic beakers (surface area 60 cm², volume 500 ml). After sowing, the beakers are filled with water up to the soil surface. 3 days after sowing, the water level is increased to slightly above soil level (3–5 mm). The application is carried out 3 days after sowing, by spraying the containers with the test substances. The dosage rate used corresponds to an amount of active substance of 500 g of A.S. per hectare. The beakers with the plants are then placed in the greenhouse under optimum growth conditions for the rice weeds, i.e. at 25°–30° C. and high atmospheric humidity.

The tests are evaluated 3 weeks after application. In these tests, the compounds of the formula I damage the weeds.

Formulation examples of active substances of the formula I (% = percent by weight)

| 1. Wettable powder | a) | b) | c) |
|---|---|---|---|
| Active substance from Table 1 | 20% | 50% | 0.5% |
| Na ligninsulfonate | 5% | 5% | 5% |
| Na lauryl sulfate | 3% | — | — |
| Na diisobutylnaphthalenesulfonate | — | 6% | 6% |
| Octylphenol polyethylene glycol ether (7–8 mol of EO) | — | 2% | 2% |
| Highly-disperse silica | 5% | 27% | 27% |
| Kaolin | 67% | — | — |
| Sodium chloride | — | — | 59.5% |

The active substance is thoroughly mixed with the additives and thoroughly ground in a suitable mill. This gives wettable powders which can be diluted with water to give suspensions of any desired concentration.

| 2. Emulsion concentrates | a) | b) |
|---|---|---|
| Active substance from Table 1 | 10% | 1% |
| Ca dodecylbenzenesulfonate | 3% | 3% |
| Octylphenol polyethylene glycol ether (4–5 mol of EO) | 3% | 3% |
| Castor oil polyethylene glycol ether (36 mol of EO) | 4% | 4% |
| Cyclohexanone | 30% | 10% |
| Xylene mixture | 50% | 79% |

Emulsions of any desired concentration can be prepared from such concentrates by diluting them with water.

| 3. Dusts | a) | b) |
|---|---|---|
| Active substance from Table 1 | 0.1% | 1% |
| Talc | 99.9% | 1% |
| Kaolin | — | 99% |

Ready-to-use dusts are obtained by intimately mixing the carrier with the active substance.

| 4. Extruder granules | a) | b) |
|---|---|---|
| Active substance from Table 1 | 10% | 1% |
| Na ligninsulfonate | 2% | 2% |
| Carboxymethylcellulose | 1% | 1% |
| Kaolin | 87% | 96% |

The active substance is mixed with the additives, and the mixture is ground and moistened with water. This mixture is extruded and subsequently dried in a stream of air.

| 5. Coated granules | |
|---|---|
| Active substance from Table 1 | 3% |
| Polyethylene glycol (MW 200) | 3% |
| Kaolin | 94% |

The kaolin is moistened with polyethylene glycol and the finely-ground active substance is applied uniformly thereto in a mixer. Dust-free coated granules are obtained in this manner.

| 6. Suspension concentrate | a) | b) |
|---|---|---|
| Active substance from Table 1 | 5% | 40% |
| Ethylene glycol | 10% | 10% |
| Nonylphenol polyethylene glycol ether (15 mol of EO) | 1% | 6% |
| Na ligninsulfonate | 5% | 10% |
| Carboxymethylcellulose | 1% | 1% |
| 37% aqueous formaldehyde solution | 0.2% | 0.2% |
| Silicone oil in the form of a 75% aqueous emulsion | 0.8% | 0.8% |
| Water | 77% | 32% |

The finely-ground active substance is mixed intimately with the additives. This gives a suspension concentrate, from which suspensions of any desired concentration can be prepared by diluting it with water.

| 7. Salt solution | |
|---|---|
| Active substance from Table 1 | 5% |

| 7. Salt solution -continued | |
|---|---|
| Isopropylamine | 1% |
| Octylphenol polyethylene glycol ether (78 mol of EO) | 3% |
| Water | 91% |

The compounds of the formula I are employed as such or preferably as compositions together with the auxiliaries customary in formulation technology, and they are therefore processed in a known manner to give, for example, emulsion concentrates, directly sprayable or dilutable solutions, dilute emulsions, sprayable powders, soluble powders, dusts, granules, and also encapsulations, for example in polymeric substances. The application methods, such as spraying, atomising, dusting, scattering or pouring, as well as the type of compositions are selected to suit the intended aims and the prevailing circumstances.

What is claimed is:

1. A compound of the formula II

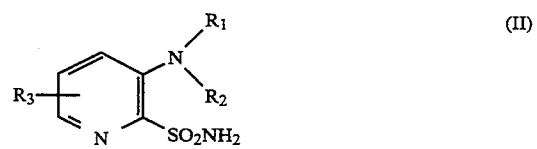

in which $R_1$ and $R_2$ independently of one another are hydrogen, $C_1-C_8$alkyl or $C_3-C_8$cycloalkyl; $C_2-C_8$alkyl or $C_3-C_8$cycloalkyl, each of which is substituted by halogen; $C_1-C_8$alkyl or $C_3-C_8$cycloalkyl, each of which is substituted by $-NR_5R_6$, $C_1-C_4$alkoxy or $C_1-C_4$alkyl$-S(O)_n-$; $C_1-C_4$alkyl or $C_3-C_6$cycloalkyl, each of which is substituted by $C_2-C_4$alkenyl, $C_5-C_6$cycloalkenyl, $C_2-C_6$alkynyl or $C_4-C_8$alkadienyl, wherein the $C_2-C_4$alkenyl, $C_5-C_6$cycloalkenyl or $C_4-C_8$alkadienyl radicals are optionally substituted by halogen; or $R_1$ and $R_2$ together are a 4–5-membered $C_4-C_{10}$alkylene chain which can be interrupted by oxygen, sulfur or $N-R_7$; $R_3$ is hydrogen, halogen, $C_1-C_4$alkyl, $C_1-C_4$alkoxy or $C_1-C_4$alkylthio; or $C_1-C_4$alkyl, $C_1-C_4$alkoxy or $C_1-C_4$alkylthio which is substituted by halogen; $R_5$, $R_6$ and $R_7$ independently of one another are hydrogen or $C_1-C_4$alkyl, and n is 0, 1 or 2; with the provisos that $R_1$, $R_2$ and $R_3$ are not simultaneously hydrogen and that $R_1$ and $R_2$ are not simultaneously hydrogen when $R_3$ is $C_1-C_4$alkyl.

2. A compound of the formula II according to claim 1, in which $R_1$ and $R_2$ independently of one another are hydrogen, $C_1-C_8$alkyl or $C_3-C_8$cycloalkyl; $C_2-C_8$alkyl or $C_3-C_8$cycloalkyl which are substituted by halogen; $C_1-C_8$alkyl or $C_3-C_8$cycloalkyl which are substituted by $-NR_5R_6$, $C_1-C_4$alkoxy or $C_1-C_4$alkyl$-S(O)_n-$; $C_1-C_4$alkyl or $C_3-C_6$cycloalkyl which are substituted by $C_2-C_4$alkenyl, $C_5-C_6$cycloalkenyl, $C_2-C_6$alkynyl or $C_4-C_8$alkadienyl, wherein the $C_2-C_4$alkenyl, $C_5-C_6$cycloalkenyl or $C_4-C_8$alkadienyl radicals are optionally substituted by halogen; or $R_1$ and $R_2$ together are a 4–5-membered $C_4-C_5$alkylene chain which can be interrupted by oxygen, sulfur or $N-R_7$.

3. A compound of the formula II according to claim 1, in which $R_1$ and $R_2$ independently of one another are hydrogen, $C_1-C_8$alkyl or $C_3-C_8$cycloalkyl; $C_2-C_8$alkyl or $C_3-C_8$cycloalkyl which are substituted by halogen; $C_1-C_8$alkyl or $C_3-C_8$cycloalkyl which are substituted by $-NR_5R_6$, $C_1-C_4$alkoxy or $C_1-C_4$alkyl$-S(O)_n-$; $C_1-C_4$alkyl or $C_3-C_6$cycloalkyl which are substituted by $C_2-C_4$alkenyl, $C_5-C_6$cycloalkenyl, $C_2-C_6$alkynyl or $C_4-C_8$alkadienyl, wherein the $C_2-C_4$alkenyl, $C_5-C_6$cycloalkenyl or $C_4-C_8$alkadienyl radicals are optionally substituted by halogen.

4. A compound of the formula II according to claim 1, in which $R_1$ and $R_2$ independently of one another are hydrogen, $C_1-C_6$alkyl or $C_3-C_6$cycloalkyl; $C_2-C_6$alkyl or $C_3-C_6$cycloalkyl which are monosubstituted to trisubstituted by halogen; $C_1-C_6$alkyl or $C_3-C_6$cycloalkyl which are substituted by $-NR_5R_6$, $C_1-C_4$alkoxy or $C_1-C_4$alkyl$-S(O)_n-$; $C_1-C_4$alkyl or $C_3-C_6$cycloalkyl which are substituted by $C_2-C_4$alkenyl, $C_5-C_6$cycloalkenyl, $C_2-C_4$alkynyl or $C_4-C_8$alkadienyl, wherein the $C_2-C_4$alkenyl, $C_5-C_6$cycloalkenyl or $C_4-C_8$alkadienyl radicals are optionally monosubstituted to trisubstituted by halogen; and $R_3$ is hydrogen, halogen, $C_1-C_4$alkyl, $C_1-C_4$alkoxy or $C_1-C_4$alkylthio; or $C_1-C_4$alkyl, $C_1-C_4$alkoxy or $C_1-C_4$alkylthio which are monosubstituted to trisubstituted by halogen.

5. A compound of the formula II according to claim 1, in which $R_3$ is in the 6-position of the pyridine ring.

6. A compound of the formula II according to claim 1, in which $R_3$ is hydrogen.

7. A compound of the formula II according to claim 1, in which $R_2$ and $R_3$ are hydrogen and $R_1$ is $C_1-C_6$alkyl or $C_3-C_6$cycloalkyl; $C_2-C_6$alkyl or $C_3-C_6$cycloalkyl which are monosubstituted to trisubstituted by halogen; $C_1-C_6$alkyl or $C_3-C_6$cycloalkyl which are substituted by $-NR_5R_6$, $C_1-C_4$alkoxy or $C_1-C_4$alkyl$-S(O)_n-$; $C_1-C_4$alkyl or $C_3-C_6$cycloalkyl which are substituted by $C_2-C_4$alkenyl, $C_5-C_6$cycloalkenyl, $C_2-C_4$alkynyl or $C_4-C_8$alkadienyl, wherein the $C_2-C_4$alkenyl, $C_5-C_6$cycloalkenyl or $C_4-C_8$alkadienyl radicals are optionally monosubstituted to trisubstituted by halogen.

8. A compound of the formula II according to claim 1, in which $R_1$ is $C_1-C_6$alkyl, allyl or propargyl, and $R_2$ is hydrogen, methyl or allyl.

9. 3-n-Butylaminopyridin-2-ylsulfonamide according to claim 7.

* * * * *